United States Patent [19]

Wilder et al.

[11] Patent Number: 4,605,990
[45] Date of Patent: Aug. 12, 1986

[54] SURGICAL CLIP-ON LIGHT PIPE ILLUMINATION ASSEMBLY

[76] Inventors: Joseph R. Wilder, 151 W. 86th St., Apt. 9D, New York, N.Y. 10024; Franklin G. Reick, 228 West Pl., Westwood, N.J. 07675

[21] Appl. No.: 653,717

[22] Filed: Sep. 24, 1984

Related U.S. Application Data

[63] Continuation-in-part of Ser. No. 612,149, Jan. 21, 1984, Pat. No. 4,562,832.

[51] Int. Cl.⁴ .............................................. F21V 8/00
[52] U.S. Cl. ..................................... 362/32; 128/20; 24/507
[58] Field of Search .................... 362/32; 24/457, 489, 24/499, 507; 128/18, 20, 303.1; 138/DIG. 8

[56] References Cited

U.S. PATENT DOCUMENTS

| | | | |
|---|---|---|---|
| 2,531,003 | 11/1950 | Slaker | 24/507 X |
| 3,641,332 | 2/1972 | Reick et al. | 362/32 |
| 3,923,372 | 12/1975 | Roland | 362/32 X |
| 4,175,306 | 11/1979 | Bigelow et al. | 24/507 |
| 4,234,910 | 11/1980 | Price | 362/32 X |
| 4,411,490 | 10/1983 | Daniel | 362/32 X |

*Primary Examiner*—Willis R. Wolfe
*Attorney, Agent, or Firm*—Michael Ebert

[57] ABSTRACT

A disposable surgical clip-on light pipe illumination assembly constituted by a manually-operated clamp adapted to clip onto an abdominal or other tissue wall surrouding a surgical site. The clamp is provided with a holder to retain a short, flexible light pipe at a position at which the front section of the pipe which terminates in an optical outlet projects into the surgical site. The rear end of the pipe terminates in an optical inlet coupled to a light source whereby light transmitted through the pipe is discharged from its optical outlet into the site. The front section of the pipe is sheathed in a bendable sleeve having dead soft characteristics, thereby making it possible for the surgeon, by bending the sleeve, to orient the light outlet to direct the light emanating therefrom toward a desired region of the surgical site.

7 Claims, 7 Drawing Figures

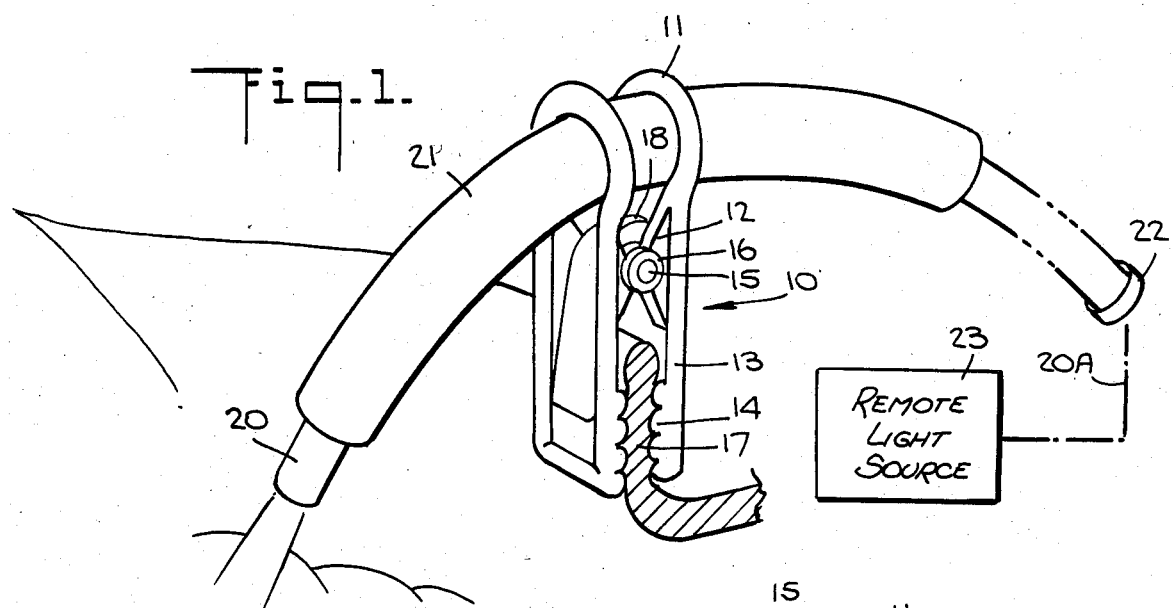
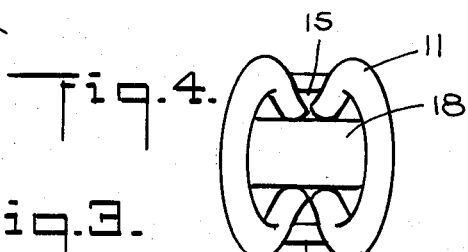
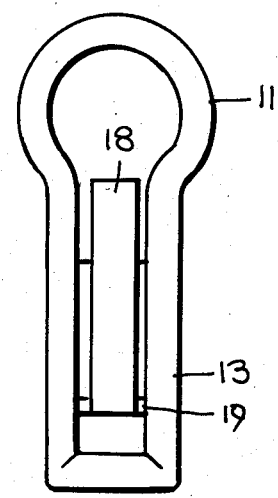
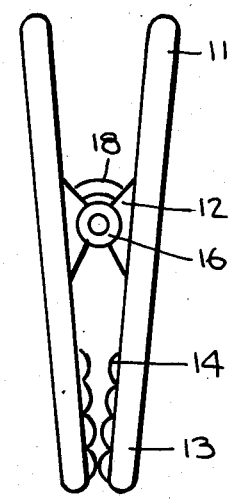
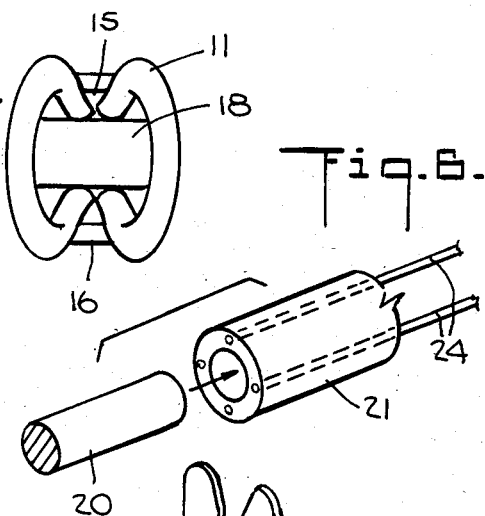
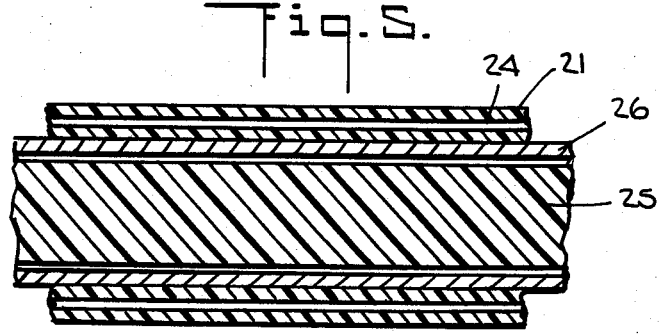
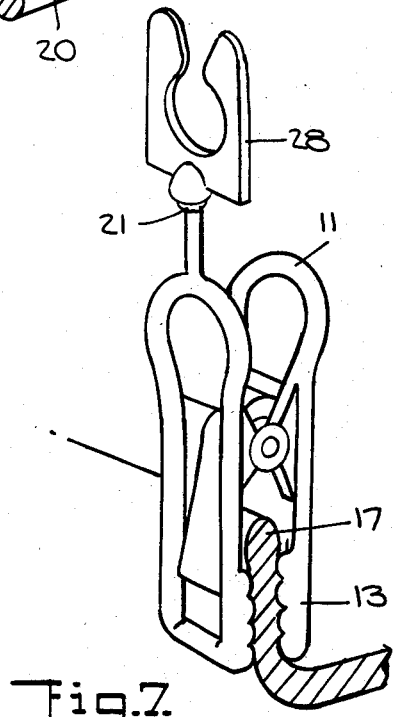

SURGICAL CLIP-ON LIGHT PIPE ILLUMINATION ASSEMBLY

RELATED APPLICATION

This application is a continuation-in-part of our copending patent application Ser. No. 612,149, filed Jan. 21, 1984, entitled "Medical Instrument and Light Pipe Illumination Assembly," now U.S. Pat. No. 4,562,832, whose entire disclosure is incorporated herein by reference.

BACKGROUND OF INVENTION

Field of Invention

This invention relates generally to devices usable in surgical procedures to illuminate a region of interest, and more particularly to a disposable clip-on light pipe illumination assembly in which the front section of the light pipe which projects into the surgical site is orientable to illuminate any region of interest to the surgeon.

Though the invention will be described mainly in the context of surgical applications, it is to be understood that the invention is not limited thereto, for an assembly in accordance with the invention is capable of transmitting light of high intensity by means of an orientable light pipe to remote or inaccessible work sites which are difficult to illuminate by conventional techniques.

The professional concern of doctors and surgeons is with body cavities and surgical sites which, unless clearly visible, cannot be properly diagnosed or treated. Existing techniques for illuminating such regions are often inadequate and unsafe, for they either do not succeed in supplying sufficient illumination or they generate excessive amounts of heat which may injure human tissue as well as cause discomfort to the observer. In some instances, commercially available illuminators interfere with medical procedures and also constitute a hazard to both patient and doctor.

The standard operating room illuminator is constituted by batteries of explosion-proof spot lamps and floor lamps, which are capable of being shifted or aimed to suit particular procedures. Such illuminators, which are quite costly, are not only cumbersome, but they fail to afford adequate illumination for deep cavities, in that the light sources are above or behind the surgeons or other operating personnel, whose heads, hands and instruments, as they shift position, often block the light rays.

In recent years, attempts have been made to use long, flexible fiber optics light guides in medical and related applications. Such guides are advantageous in that they furnish "cold light" and segregate the heavy and bulky assembly of lamp, condenser and cooling system from the point of observation. Also, with the development of flexible fiber optic guides with fused ends and plastic casings, sterilization of the instrument is possible.

In its preferred form, a clip-on assembly in accordance with the present invention includes a flexible light guide in a monofilament-core pipe format. This represents a particular species of an optical fiber. It is important, therefore, that the distinctions which exist between a conventional multi-fiber optical light pipe or cable and a light pipe having a monofilament-core be clearly understood.

An optical fiber is a dielectric waveguide structure which functions by internal reflection to confine and guide light. It consists of an inner dielectric material, called the core, surrounded by another dielectric material having a smaller refractive index, referred to as the cladding. Currently, all optical fibers in general use have a cylindrical circular cross section.

The amount of light flux which an optical fiber is capable of conveying depends on the cross-sectional diameter of the core; and when there is a need to transmit large amounts of light at a constant level for purposes of illumination, rather than a modulated light signal for purposes of communication, use is usually made of a bunched cluster of optical fibers, each conveying a small amount of light.

Since the present invention is concerned primarily with illumination, it employs a light guide in the form of a flexible pipe having a monofilament-core of large diameter surrounded by a cladding tube. The monofilament core serves the same function as a cluster of small diameter cores, but operates with far greater optical efficiency to transmit large amounts of light with minimal transmission losses. It is also more bendable than conventional multi-filament core light pipes.

Fiber optic guides may be used as auxiliary illuminators for close diagnostic and surgical operations, as illuminators for direct or indirect ophthalmoscopes, and as specially shaped illumination accessories to classical-designed cytoscopes, proctoscopes, retractors, and various forms of medical, surgical and dental tools.

Despite the obvious advantages of fiber optics for cold-light illumination, their use in the surgical, medical and dental fields has been relatively limited. The reason for such limited use does not lie in any inherent theoretical deficiency, but in the fact that with existing technology, the three basic components of the fiber optics system, when brought together, do not afford sufficient illumination in those situations calling for large amounts of cold light which can be readily directed to selected regions of a body cavity.

In our copending patent application, above-identified, a medical instrument and light pipe assembly is disclosed which makes use of a flexible plastic light pipe whose monofilament core is surrounded by a cladding tube, the light pipe being joined to an instrument such as a surgical retractor which, when put to use, assumes a position in which its operative blade lies adjacent to the field of interest, such as a body cavity or surgical site.

The optical inlet at the rear end of the light pipe is coupled to a light source whereby light transmitted by the pipe is discharged from an optical outlet at the front section of the pipe which is adjacent to the blade of the retractor. The front section of the pipe is sheathed in a bendable neck having dead soft characteristics whereby the user, by bending the neck, may so orient the optical outlet as to direct the light toward a desired region of the surgical site.

In the assembly disclosed in our copending application, the specially-designed molded plastic retractor included in the assembly is provided with clips or other routing means to link the retractor to the flexible light pipe; hence standard retractors cannot be used for this purpose.

Most hospital facilities carry a large inventory of standard retractors of different types, and these are often put to use in surgical procedures. Though distinct advantages may be gained by replacing standard retractors with the specially-designed retractors disclosed in our copending application, which are combined with orientable light pipe illuminators, practical considerations dictate the need for an independent device capable of exploiting these orientable illuminators for use in conjunction with standard surgical retractors.

In this way, surgeons can continue to carry out procedures with available retractors and other conventional instruments and yet take advantage of the enhanced and unobstructed illumination afforded by spilling light directly onto the surgical site, rather than drawing light from overhead sources which may be more or less occluded by personnel working in the vicinity of the surgical site.

The prior art patent of greatest interest is the Reick-Wilder Pat. No. 3,641,332, which discloses a flexible light pipe constituted by a monofilament core of resinous material of large diameter, such as methyl methacrylate contained within a cladding tube formed of FEP (Teflon), the core being separated from the tube by a film of air. The core has a relatively high index of refraction capable of transmitting light by internal reflectors, whereas the cladding tube has a relatively low refractive index.

SUMMARY OF INVENTION

In view of the foregoing, the main object of this invention is to provide a light pipe illumination assembly adapted to clip onto an abdominal or other tissue wall surrounding a surgical site, the front section of the pipe being orientable to direct light toward a region of interest.

While the assembly, when used in surgery, is clipped onto a tissue wall, the same assembly, when used in other applications requiring direct illumination, may be clipped onto whatever wall or other stable member is available at the work site.

More specifically, it is an object of the invention to provide an assembly composed of a manually-operated plastic clamp and a short length of light pipe made of synthetic plastic material whereby the entire assembly is inexpensive and is disposable after a single use, thereby dispensing with the need to clean and resterilize the assembly.

Briefly stated, these objects are attained in disposable surgical clip-on light pipe illumination assembly constituted by a manually-operated clamp adapted to clip onto an abdominal or other tissue wall surrounding a surgical site. The clamp is provided with a holder to retain a short, flexible light pipe at a position at which the front section of the pipe which terminates in an optical outlet projects into the surgical site. The rear end of the pipe terminates in an optical inlet coupled to a light source whereby light transmitted through the pipe is discharged from its optical outlet into the site. The front section of the pipe is sheathed in a bendable sleeve having dead soft characteristics, thereby making it possible for the surgeon, by bending the sleeve, to orient the light outlet to direct the light emanating therefrom toward a desired region of the surgical site.

OUTLINE OF DRAWINGS

For a better understanding of the invention as well as other objects and further features thereof, reference is made to the following detailed description to be read in conjunction with the accompanying drawings, wherein:

FIG. 1 is a perspective view of a clip-on assembly in accordance with the invention;

FIG. 2 is an end view of the clamp included in the assembly;

FIG. 3 is a side view of the clamp;

FIG. 4 is a top view of the clamp;

FIG. 5 is a longitudinal section taken through the front section of the light pipe and the bendable sleeve surrounding the front section to render it orientable;

FIG. 6 is a preferential view of the sleeve; and

FIG. 7 is another embodiment of a clamp for use in conjunction with the light pipe.

DESCRIPTION OF INVENTION

Referring now to FIGS. 1 to 3, an assembly in accordance with the invention is constituted by a light pipe to provide direct and orientable illumination at a surgical site, joined to a manually-operated clamp having a pair of complementary pieces, generally designed by numeral 10, the clamp being formed entirely of synthetic plastic material of good strength such as polypropylene.

Each piece includes a loop-shaped handle 11 having a circular opening, an intermediate trunnion 12 having an arcuate slot, and a flat jaw 13 whose inner surface 14 is corrugated to prevent slippage when the jaws are clamped onto tissue wall 17.

Received within the complementary arcuate slots of trunnion 12 is a pivot tube 15 having end flanges 16 to prevent axial displacement thereof, the pieces being swingable relative to each other so that the jaws may be opened and closed. The pieces are held together by a U-shaped spring 18 of resilient plastic material whose yoke is seated on the pivot tube, the depending arms of the spring engaging the flat outer surfaces of jaws 13 and terminating in detents which snap into notches 19 in these outer surfaces. Spring 18 acts to normally bias the jaws toward each other; but when the handles are pressed together, the jaws swing apart to permit their engagement with a tissue wall.

The clamp serves as an anchor for a flexible plastic light pipe of short length, generally designated by numeral 20. The front section of light pipe 20 is sheathed in a bendable tubular sleeve 21. The sheathed front section is threaded through the loop openings of the handles 11 of the clamp, as shown in FIG. 1, and projects therefrom onto the surgical site. Thus the looped handle of the clamp also functions as the holder for the light pipe, hence the diameter of the loop openings must be appropriate to that of the ensheathed front section of the light pipe.

The rear end of light pipe 20 forms an optical inlet and terminates in an optical connector 22, preferably of plastic construction, adapted to couple the short light pipe to a high-intensity light source 23 by way of an extension line 20A. This line may be a long light pipe of the same type as the short pipe 20 so that the light source which is electrically powered is at a safe distance from the operating table and beyond the sterile field. In practice, the light source may be of the type disclosed in the above-identified Reick-Wilder patent, whose entire disclosure is incorporated herein by reference.

The bendable sleeve 21 may be of the type disclosed in our copending application and be made of thin tubular material, such as aluminum, which has dead soft characteristics and is altogether without memory, so that when the sleeve is manually bent and then released, it retains its deformed state without springing back. The sleeve may be formed by a spiral of metal stripping. Hence when the retractor and light pipe assemblies are in use at a surgical site, as shown in FIG. 1, light from the source is transmitted through the light pipe and projected from the optical outlet end thereof into the surgical site. Since in the course of a surgical procedure, the surgeon may wish to concentrate the light on a particular region in the site, in order to do so, he has only to bend the light director sleeve so as to orient the outlet end of the pipe in the desired direction, the sleeve then acting in a manner comparable to a goose neck. And this bending action of the sleeve may be carried out repeatedly as other regions require illumination in the course of a procedure.

A preferred form of sleeve 21 is shown in FIG. 6, where it will be seen that the sleeve is formed of a tube of flexible foam plastic material having embedded therein an array of longitudinally-extending wires 24 of copper, lead or other metal having dead soft characteristics. The advantage of a foam plastic sleeve of this type is that the sleeve through which the front section of the light pipe is telescoped is compressible and can be dimensioned with respect to the loop handles of the clamp so as to be compressed within the loops to ensure a stable coupling to the clamp holder. As shown in FIG. 5, light pipe 20 has a plastic core 25 of high refractive index surrounded by a cladding tube 26 of lower refractive index separated by a thin air film from the core.

As pointed out in the above-identified Reick-Wilder patent, the ideal light guide has a core of the highest possible refractive index in combination with a cladding of the lowest possible refractive index. Commercially-available light pipes, such as the "CROFON" pipe made by DuPont, falls far short of this ideal, for this pipe makes use of a polymethyl methylacrylate core in a polyethylene cladding tube.

Polyethylene has a refractive index of 1.54, as compared to air, whose index is 1.0. However, though air has the lowest possible refractive index, air normally cannot serve as a cladding, for, if unconfined, it is incapable of protecting the core from scratches and contamination which degrade its quality. In the Reick-Wilder light pipe, one still has a protective plastic outer tube (Teflon); but it is the inner air film, except at those limited points where the core makes physical contact with the tube, which acts effectively as a cladding having the lowest possible refractive index. At those points where the core touches the Teflon tube, internal reflection will still take place, for Teflon has a refractive index of about 1.34 which is lower than that of the core and therefore functions as a cladding, though this cladding is less effective than air.

Thus the light pipe 20 and core adjacent the surgical site act to transmit light efficiently from the source to the optical outlet and to spill the light onto the site. Since the front section of the pipe is readily orientable and will maintain the bend imparted thereto, the surgeon, as the need arises in the course of a procedure, may reorient the front section to illuminate whatever region of the site is of interest.

In some instances, it may be desirable to provide means on the clamp to permit a gross adjustment of the light pipe so that it can be quickly oriented in the desired direction and then further oriented by bending the front section. To this end, as shown in FIG. 7, the clamp has a universal joint 27 attached thereto provided with a holder 28 to receive the front section of the light pipe. The universal joint is in the form of a ball clamped between a pair of resilient blades. In this way the surgeon can, by adjustment of the joint, orient the front section of the light pipe in the general direction of the region of interest and by bending the front section orient the light beam more precisely.

While there has been shown and described a preferred embodiment of CLIP-ON LIGHT PIPE ILLUMINATION ASSEMBLY in accordance with the invention, it will be appreciated that many changes and modifications may be made therein without, however, departing from the essential spirit thereof.

Thus, instead of a universal joint attached to the clip-on clamp as shown in FIG. 7 to provide a holder for the light pipe permitting gross adjustment thereof, use may be made of a pipe holder having a pipe-holding section and a snap-in section in the form of a round, resilient plastic button which snaps into one of the circular handle loops of the clamp shown in FIG. 2, whereby the button may be turned within the loop to angularly shift the position of the front section of the light pipe.

In dental applications, the clamp for the light pipe may be designed to clip onto the teeth or lip of the patient adjacent the work site, or it may be adapted to clip onto an adjustable mechanical arm adjacent the oral cavity.

We claim:

1. A light pipe illumination assembly to illuminate a work site, said assembly comprising:
   A. a light pipe having an optical outlet at its front end and an optical inlet at its rear end, said rear end having means to couple the pipe to a light source;
   B. detachable means to anchor said pipe adjacent the work site at a position in which the front section cantilevers form the anchor means into the site; and
   C. a bendable sleeve surrounding the front section having dead soft characteristics to render the front section orientable.

2. A surgical clip-on light pipe illumination assembly comprising:
   A. a manually-operated clamp adapted to clip onto an abdominal or other tissue wall surrounding a surgical site without damage thereto, said clamp being provided with a light pipe holder; and
   B. a short, flexible light pipe formed of a plastic monofilament having a high refractive index surrounded by a cladding tube of lower refractive index and having an optical inlet at its rear end and an optical outlet at its front end, said pipe being retained by the holder at a position at which the front section of the pipe whose front end forms said optical outlet cantilevers from the holder into the surgical site, said front section being ensheathed in a bendable sleeve having dead soft characteristics to orient said optical outlet to adjust the direction of the light beam and to maintain it at its adjusted orientation, the optical inlet of the pipe being coupled to a remote light source whereby the light transmitted through the pipe is discharged from the optical outlet to produce a light beam which is directable into the surgical site to illuminate any region of interest.

3. An assembly as set forth in claim 2, wherein said holder is coupled to the clamp through a universal joint.

4. An assembly as set forth in claim 2, wherein said sleeve is formed of a tube of flexible foam plastic material having at least one wire of dead soft material embedded therein.

5. An assembly as set forth in claim 4, wherein said sleeve has embedded therein an array of longitudinally-extending wires.

6. An assembly as set forth in claim 2, wherein said clamp is formed by a pair of pieces each having a handle at one end and a jaw at the other end, the pieces being pivotally connected and spring-biased, whereby the jaws normally engage each other and are separated by pressing the handles together.

7. An assembly as set forth in claim 6, wherein said handles are in loop form, whereby the pipe may be extended through the loop openings and the handles also function as the holder.

* * * * *